United States Patent [19]

Sitzmann

[11] Patent Number: 5,081,255

[45] Date of Patent: Jan. 14, 1992

[54] HIGH MELTING AROMATIC NITRATE ESTERS

[75] Inventor: Michael E. Sitzmann, Adelphi, Md.

[73] Assignee: The United States of America as represented by the Secretary of the Navy, Washington, D.C.

[21] Appl. No.: 704,561

[22] Filed: May 17, 1991

[51] Int. Cl.$^5$ .............................................. C07D 413/00
[52] U.S. Cl. .................................... 548/145; 558/484
[58] Field of Search ................ 558/480, 482, 483, 484, 558/485; 548/145

[56] References Cited

U.S. PATENT DOCUMENTS

| | | | |
|---|---|---|---|
| H644 | 6/1989 | Sitzmann et al. | 558/483 |
| 3,228,929 | 1/1966 | Frankel | 558/485 |
| 3,278,578 | 10/1966 | Frankel | 558/485 |

OTHER PUBLICATIONS

Tarasova et al., Zh. Org. Khim., 1985, 21(11), 2260-3 CA 105:42065s.

Primary Examiner—Robert L. Stoll
Assistant Examiner—Chhaya Sayala
Attorney, Agent, or Firm—Kenneth E. Walden; Roger D. Johnson

[57] ABSTRACT

A nitrate ester which is 2,4,6-trinitro-1-(2-hydroxyethylamino)-3- (2-hydroxyethylnitramino)benzenedinitrate; 2,4,6-trinitro-1,3,5-tris(2-hydroxyethylamino)benzenetrinitrate; 2,2',4,4',6,6'-hexanitro-3-(2-hydroxyethylnitramino)stilbenitrate; 2,5-bis[3-(hydroxyethylaminonitrate)-2,4,6-trinitrophenyl]1,3,4-oxadiazole; or 2,5-bis[3-(hydroxyethylaminonitrate)-5- (hydroxyethylnitraminonitrate)-2,4,6-trinitrophenyl]-1,3,4-oxiazole and a process for preparing these compounds.

6 Claims, No Drawings

HIGH MELTING AROMATIC NITRATE ESTERS

BACKGROUND OF THE INVENTION

This invention relates to organic nitrate esters and more particularly to aromatic nitrate esters which are useful as explosives.

The availability of high-melting nitrate esters is very limited. Pentaerythritol tetranitrate (PETN) is the highest melting of commonly available nitrate esters, but its melting point (140° C.) precludes its use at temperatures in the vicinity of 150° C. and above [missile systems often require explosives that can withstand short-term (30 minutes) exposure to temperatures in the vicinity of 150° C. and above due to aerodynamic heating]. A higher melting (mp 158°-160° C.) nitrate ester, 2,4,6-trinitro-1,3,5-tris(2-hydroxyethylnitramino)benzenetrinitrate, has been reported but its availability is limited by procedures that provide low to moderate yields (approximately 50%). Thus, it would be advantageous to have available a method that provides high yields of high-melting nitrate esters to allow a wide range of melting points and sensitivities as well as short-term stability at 150° C.

SUMMARY OF THE INVENTION

Accordingly, an object of this invention is to provide novel, high-melting nitrate esters.

Another object of this invention is to provide nitrate esters that have short term stability in the vicinity of 150° C.

A further object of this invention is to provide high-melting nitrate esters with a wide range of melting points and sensitivities for use as initiation train explosives and/or as booster explosives.

These and other objects of this invention are accomplished by providing a nitrate ester which is 2,4,6-trinitro-1-(2- hydroxyethylamino)-3-(2-hydroxyethylnitramino)benzenedinitrate; 2,4,6-trinitro-1,3,5-tris(2-hydroxyethylamino)benzenetrinitrate; 2,2',4,4',6,6'-hexanitro-3-(2-hydroxyethylnitramino)stilbenenitrate; 2,5-bis[3-(hydroxyethylaminonitrate)-2,4,6-trinitrophenyl-]1,3,4-oxadiazole; or 2,5-bis[3-(hydroxyethylaminonitrate)-5-(hydroxyethylnitraminonitrate)-2,4,6-trinitrophenyl]-1,3,4-oxadiazole.

The nitrate esters are produced by first reacting the appropriate amount of ethanolamine with a chlorine or methoxy substituted polynitro aromatic compound which is (1) 2,4-dichloro-1,3,5-trinitrobenzene;
(2) 2,4,6-trinitro-1,3,5-trichlorobenzene;
(3) 3-chloro-2,2',4,4',6,6'-hexanitrostilbene;
(4) 2,5-bis(3-methoxy-2,4,6-trinitrophenyl)-1,3,4-oxadiazole; or
(5) 2,5-bis(3,5-dimethoxy-2,4,6-trinitrophenyl)-1,3,4-oxadiazole to produce the corresponding hydroxyethylamino substituted compound (1) 2,4,6-trinitro-1,3-bis(2-hydroxyethylamino)benzene;
(2) 2,4,6-trinitro-1,3,5-tris(2-hydroxyethylamino)benzene;
(3) 2,2',4,4',6,6'-hexanitro-3-(2-hydroxyethylamino)stilbene;
(4) 2,5-bis(3-hydroxyethylamino-2,4,6-trinitrophenyl)-1,3,4-oxadiazole; or
(5) 2,5-bis[3,5-bis(hydroxyethylamino)-2,4,6-trinitrophenyl]-1,3,4-oxadiazole which is then control nitrated by using 90% nitric acid at a temperature of from about −25° C. to 0° C. to form the corresponding nitrate ester (1) 2,4,6-trinitro-1-(2-hydroxyethylamino)-3-(2hydroxymethylnitramino)benzenedinitrate:
(2) 2,4,6-trinitro-1,3,5-tris(2-hydroxyethylamino)benzenetrinitrate:
(3) 2,2',4,4',6,6'-hexanitro-3-(2-hydroxyethylnitramino)stilbenenitrate
(4) 2,5-bis[3-(hydroxyethylaminonitrate)-2,4,6trinitrophenyl]-1,3,4-oxadiazole; or
(5) 2,5-bis[3-(hydroxyethylaminonitrate)-5-droxethylnitraminonitrate)-2,4,6-trinitrophenyl]-1,3,4-oxadiazole.

These high melting nitrate esters can withstand temperatures in the vicinity of 150° C. or above without melting or undergoing significant decomposition. These nitrate esters are suitable for use as initiator train or booster explosives for use in high temperature environments such as missiles.

DETAILED DESCRIPTION OF THE PREFERRED EMBODIMENT

The explosive compounds of this invention are the following high-melting polynitroaromatic nitrate esters:

(I) 2,4,6-trinitro-1-(2-hydroxyethylamino)-3-(2-hydroxyethylnitramino) benzenedinitrate (mp 146-148° C.),

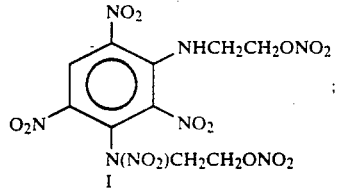

I (II) 2,4,6-trinitro-1,3,5-tris(2-hydroxyethylamino) benzenetrinitrate (mp 186° C. dec.),

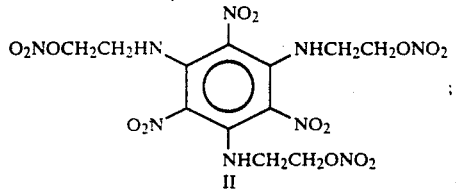

II (III) 2,2',4,4',6,6'-hexanitro-3-(2-hydroxyethylnitramino)
stilbenenitrate (mp 197° C. dec.)

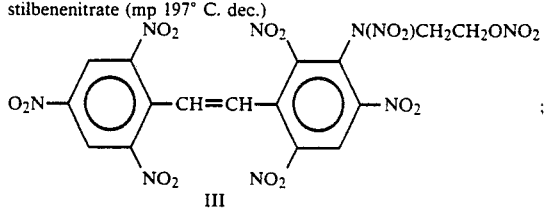

III (IV) 2,5-bis[3-(hydroxyethylaminonitrate)-2,4,6-trinitrophenyl]-
1,3,4-oxadiazole (mp 206° C. dec),

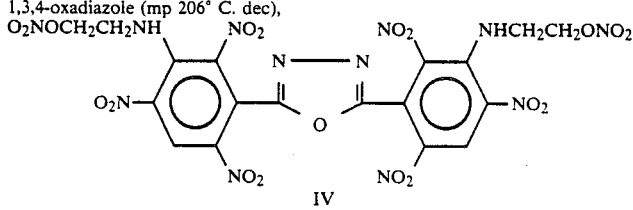

IV (V) 2,5-bis[3-(hydroxyethylaminonitrate)-5-(hydroxyethylnitraminonitrate)-
2,4,6-trinitrophenyl]-1,3,4-oxadiazole (mp 193° C. dec),

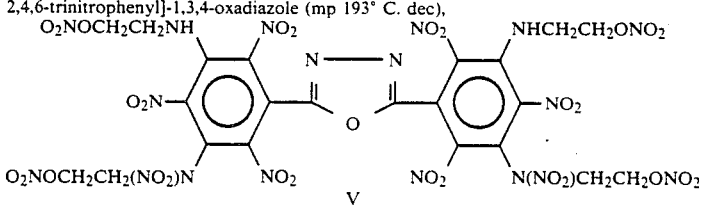

V

The melting points of nitrate esters (I-V) range from 146° C. to 206° C. and their impact sensitivities (ERL machine, Type-12 tools on sandpaper) range from 13 cm to 61 cm. These properties, along with oxidant balance ($OB_{100}$), are shown in table 1.

TABLE 1

| PROPERTIES OF NITRATE ESTERS (I-V) | | | |
|---|---|---|---|
| COMPOUND | M.P. °C. | $H_{50\%}(cm)^{(a)}$ | $OB_{100}^{(b)}$ |
| I | 146 | 20 | −0.43 |
| II | 186 | 43 | −1.71 |
| II (FINE) | 186 | 23 | −1.71 |
| III | 197 | 61 | −1.17 |
| IV | 206 | 13 | −1.43 |
| V | 193 | 27 | −0.40 |

$^{(a)}$RDX = 16-20 cm.
$^{(b)}$For reference: TNT = −3.08; TATB = −2.33; HNS = −2.22; TETRYL = −1.04.

The oxidant balance ($OB_{100}$) was calculated by the method taught by M. J. Kamlet and H. G. Adolph, Proceedings of Seventh Symposium (International) on Detonation, June 16-19, 1981, Annapolis, Md., page 85. Oxidant balance ($OB_{100}$) is defined as the number of equivalents of oxidant per 100 grams of explosive above the amount required to burn all hydrogen to $H_2O$ and HF and all carbon to CO and is represented by the equation, $$OB_{100} = \frac{100(2n_O + n_F - n_H - 2n_C - 2n_{COO})}{\text{molecular weight}}$$

where $n_O$, $n_F$, $n_H$, and $n_C$ represent the number of atoms of the respective elements in the molecule, and $n_{COO}$ is the number of carboxy groups.

Compounds II-V exhibit good short-term stability at 150° C. There was little, if any, change in melting points for these compounds after they were held at 150° C. for 1 hr. Compound IV was held isothermally at 150° C. for 5 hr. in a differential scanning calorimeter. There was no evidence of decomposition and the recovered material was unchanged according to thin layer chromatography. This demonstrates the value of these nitrate esters in short-term high temperature applications such as explosive trains or booster explosives in missiles.

The nitrate esters of this invention are prepared in a two step process. In the first step, ethanolamine, $NH_2CH_2CH_2OH$, is reacted with one of the following chlorine or methoxy substituted polynitro aromatic compounds:

(IA) 2,4-dichloro-1,3,5-trinitrobenzene;

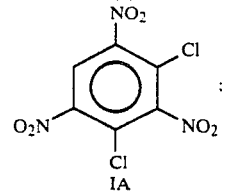

IA (IIA) 2,4,6-trinitro-1,3,5-dichlorobenzene,

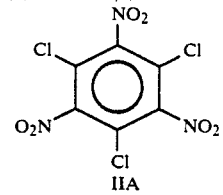

IIA (IIIA) 3-chloro-2,2',4,4',6,6'-hexanitrostilbene,

-continued

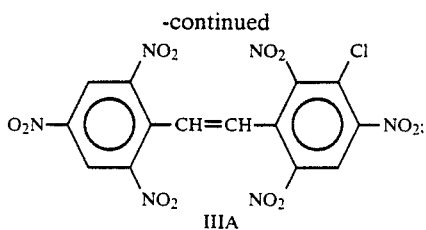
IIIA (IVA) 2,5-bis(3-methoxy-2,4,6-trinitrophenyl)-1,3,4-oxadiazole,

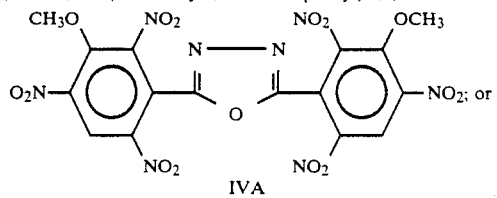
IVA (VA) 2,5-bis(3,5-dimethoxy-2,4,6-trinitrophenyl)-1,3,4-oxadiazole,

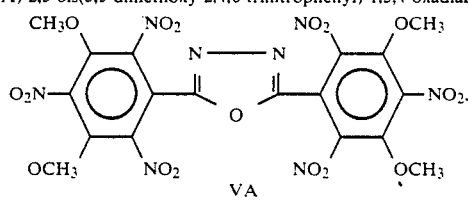
VA in a suitable solvent such as methanol. Preferably a stoichiometric amount of ethanolamine is used in the reaction with methoxy groups, but preferably a stoichiometric excess of ethanolamine is used in the reaction with chloro groups. Preferably the reactants are mixed together slowly with cooling and agitation to prevent localized heating from the reaction. After the reactants are mixed they are preferably allowed to react at ambient (room) temperature. The reactions produce the corresponding hydroxyethylamine, —NHCH$_2$CH$_2$OH, substituted polynitro aromatic compounds:

(IB) 2,4,6-trinitro-1,3-bis(2-hydroxyethylamino)benzene.

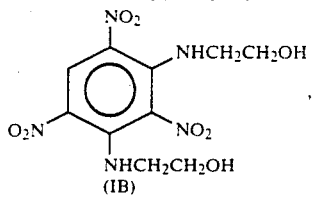

see example 1;

(IIB) 2,4,6-trinitro-1,3,5-tris(2-hydroxyethylamino)benzene.

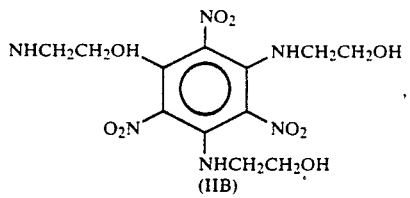

see example 3;

(IIIB) 2,2′,4,4′,6,6′-hexanitro-3-(2-hydroxyethylamino)stilbene.

-continued

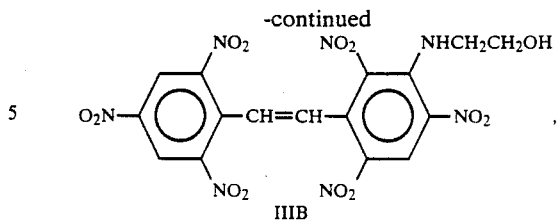
IIIB see example 5;

(IVB) 2,5-bis(3-hydroxyethylamino-2,4,6-trinitrophenyl)-1,3,4-oxadiazole.

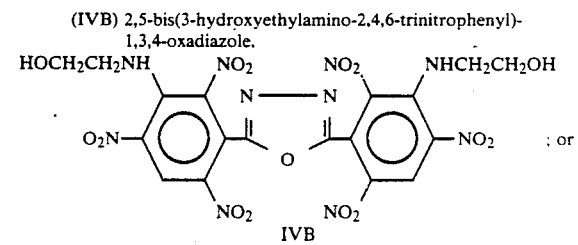
IVB see example 7; or (VB) 2,5-bis[3,5-bis(hydroxyethylamino)-2,4,6-trinitrophenyl]-1,3,4-oxadiazole.

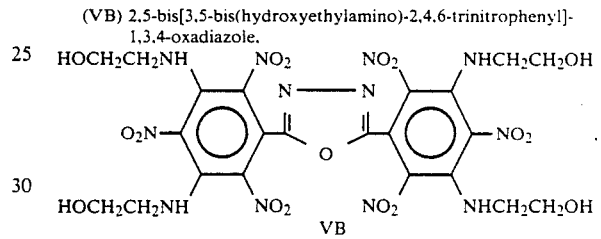
VB see example 12.

The intermediary product I B, IIB, IIIB, IVB, or VB, is separated from the reaction mixture and purified for use in the nitrate ester formation step. The high melting nitrate esters of this invention (I, II III, IV, and V) are provided by the controlled nitration of the polynitroaromatic compounds containing —NHCH$_2$CH$_2$OH substituents (I B, IIB, IIIB, IVB, or VB, respectively). The controlled nitration is achieved by using 90% nitric acid at temperatures from −25° C. to 0° C. The object is to produce —NHCH$_2$CH$_2$ONO$_2$ substituents and limit the number of —NNO$_2$CH$_2$CH$_2$ONO$_2$ substituents formed. The —NH(CH$_2$)$_2$ONO$_2$ substituent is desired for its ability to increase melting points and stabilities relative to —NNO$_2$(CH$_2$)$_2$ONO$_2$. The general equation for this new method is:

$$R[NH(CH_2)_2OH]_n \xrightarrow[0° C. \text{ to } -25° C.]{90\% \text{ HNO}_3}$$

$$R[NH(CH_2)_2ONO_2]_m[NNO_2(CH_2)_2ONO_2]_{n-m}$$

where R is the polynitroaromatic moiety. Table 2 summarizes the examples illustrating this nitration step.

TABLE 2

| starting compound | nitrate ester product | example |
|---|---|---|
| IB | I | 2 |
| IIB | II | 4 |
| IIIB | III | 6 |
| IVB | IV | 8 |
| VB | V | 13 |

Compound III was formed even at temperatures in the vicinity of −50° C. and control of nitration to form the —NH(CH$_2$)$_2$ONO$_2$ compound was not achieved. However, the melting point of III (197° C.) is sufficiently high that it is useful as a high melting nitrate ester.

The general nature of the invention having been set forth, the following examples are presented as specific illustrations thereof. It will be understood that this invention is not limited to these specific examples, but is susceptible to various modifications that will be recognized by one of ordinary skill in the art.

EXAMPLE 1

2,4,6-trinitro-1,3-bis(2-hydroxyethylamino)benzene

To 25 ml of methanol stirred in an ice bath was added 2.8 g (0.01 mole) of 2,4-dichloro-1,3,5-trinitrobenzene followed by the addition of a solution of 2.6 g (0.042 mole) of ethanolamine in methanol (25 ml) over 10 min. After 2.5 hr. at room temperature, the mixture was filtered to give 2.8 g (85%) of yellow crystals, mp 200°–202° C. The literature method gives 50% yield, mp 203°–205° C. $^1$H NMR (DMSO-d$_6$+D$_2$O): 3.15 (t, 4H), 3.65 (t, 4H), 9.14 (s, 1H). The title compound can be prepared similarly by treating the dimethoxy compound, 2,4-dimethoxy-1,3,5-trinitrobenzene, with ethanolamine in methanol.

EXAMPLE 2

2,4,6-trinitro-1-(2-hydroxyethylamino)-3-(2-hydroxymethylnitramino)benzenedinitrate (I)

To 90% nitric acid (5 ml) stirred in an ice bath was added 1.20 g (0.0036 mole) of 2,4,6-trinitro-1,3-bis(2-hydroxyethylamino)benzene rapidly in portions. After 5 min., the mixture (crystals have precipitated) was poured onto ice to give 1.70 g (100%) of yellow solid (mp 143°–146° C.) which after crystallization from acetone-methanol yielded 1.57 g (93%) of I, mp 146°–148° C.; $^1$H NMR (acetone-d$_6$+D$_2$O): 3.83 (t, 2H), 4.27–4.73 (m, 2H), 5.00 (m, 2H), 9.50 (s, 2H). Anal. Calcd. for C$_{10}$H$_{10}$N$_8$O$_{14}$: C, 25.76; H, 2.16; N, 24.03. Found: C, 25.94; H, 2.08; N, 23.66.

EXAMPLE 3

2,4,6-trinitro-1,3,5-tris(2-hydroxyethylamino)benzene

A mixture of 7.2 g (0.0227 mole) of 2,4,6-trinitro-1,3,5-trichlorobenzene and 70 ml of methanol was stirred in an ice bath while a solution of 9.9 g (0.162 mole) of ethanolamine in 70 ml of methanol was added over 10 min. Stirring at room temperature gave a solution from which yellow solid precipitated until the mixture became too thick to stir. After standing for 2 hr., the mixture was filtered to give 7.6 g (86%) of 2,4,6-trinitro-1,3,5-tris(2-hydroxyethylamino)benzene; $^1$H NMR (DMSO-d$_6$): 3.48 (m, 6H), 3.72 (m, 6H).

EXAMPLE 4

2,4,6-trinitro-1,3,5-tris(2-hydroxyethylamino)benzenetrinitrate (II)

Nitric acid (90%) (6 ml) was stirred in an ice bath during the addition of 1.0 g (0.00256 mole) of 2,4,6-trinitro-1,3,5-tris(2-hydroxyethylamino)benzene. After 3 min., the solution was poured onto ice to give a yellow solid which was stirred with 5 ml of boiling acetone. Methanol (10 ml) was added and the insoluble yellow solid [1.23 g(91%), mp 185° C. dec.] was removed; $^1$H NMR (DMSO-d$_6$+D$_2$O): 3.83 (t, 2H), 4.95 (t, 2H); IR (KBr): 3220 (NH), 1640 (ONO$_2$), 1590(NO$_2$). Anal. Calcd. for C$_{12}$H$_{15}$N$_9$O$_{15}$: C, 27.44; H, 2.88; N, 24.00. Found: C, 27.66; H, 2.86; N, 23.93.

EXAMPLE 5

2,2',4,4',6,6'-hexanitro-3-(2-hydroxyethylamino)stilbene

A mixture of 2.4 g (0.005 mole) of 3-chloro-2,2',4,4',6,6'-hexanitrostilbene and 30 ml of methanol was stirred in a ice bath while 0.65 g (0.0105 mole) of ethanolamine in 10 ml of methanol was added all at once. The mixture was stirred for 24 hr. at room temperature before it was filtered to give 2.5 g (99%) of yellow solid, mp 240° C.; $^1$H NMR(DMSO-d$_6$+D$_2$O): 3.22 (t, 2H), 3.60 (t, 2H), 7.15 (s, 2H), 9.12 (s, 1H), 9.27 (s, 2H).

EXAMPLE 6

2,2',4,4',6,6',-hexanitro-3-(2-hydroxyethylnitramino)-stilbenenitrate (III)

To 11 ml of 90% nitric acid stirred in an ice bath was added 2.15 g (0.0042 mole) of 2,2',4,4',6,6'-hexanitro-3-(2-hydroxyethylamino)stilbene. After 10 min. (solid has precipitated from solution), the mixture was poured onto ice to give 2.5 g (99%) of cream colored solid, mp 195° C. dec. Crystallization from acetone-methanol raised the melting point to 197° C. dec. $^1$H NMR (acetone-d$_6$): 4.70 (m, 2H), 5.02 (m, 2H), 7.15–7.72 (m, 2H), 9.35 (s, 2H), 9.48 (s, 1H). Anal. Calcd. for C$_{16}$H$_9$N$_9$O$_{17}$: C, 32.07; H, 1.51; N, 21.03. Found: C, 31.96; H, 1.25; N, 21.03.

EXAMPLE 7

2,5-bis(3-hydroxyethylamino-2,4,6-trinitrophenyl)-1,3,4-oxadiazole

A solution of 0.3 g (0.0049 mole) of ethanolamine in 20 ml of methanol was stirred in an ice bath during the addition of 1.0 g (0.0018 mole) of 2,5-bis(3-methoxy-2,4,6-trinitrophenyl)-1,3,4-oxadiazole. After 10 min. at 0° C., the mixture was stirred at room temperature for 5 hr. before the crude product [1.1 9 (94%), mp 250° dec] was removed by filtration. Digestion with boiling acetone gave the purified product, as an insoluble yellow solid, mp 264° C. dec.; $^1$H NMR (DMSO-d$_6$+D$_2$O): 3.22 (t, 4H), 3.70 (t, 4H), 9.32 (s, 2H); IR(KBr): 3700–3200 (OH and NH), 1610, 1625 (C=N), 1545, 1340 (NO$_2$). Anal. Calcd. for C$_{18}$H$_{14}$N$_{10}$O$_{15}$: C, 35.42; H, 2.31; N, 22.95. Found: C, 35.62; H, 2.30; N, 22.93.

EXAMPLE 8

2,5-bis[3-(hydroxyethylaminonitrate)-2,4,6-trinitrophenyl]-1,3,4-oxadiazole (IV)

To 40 ml of 90% nitric acid stirred at −25° C. was added 4.0 g (0.00655 mole) of crude 2,5-bis(3-hydroxyethylamino-2,4,6-trinitrophenyl)-1,3,4-oxadiazole over 2 min. The solution was held at −25° C. for 5 min. before it was poured onto ice to give 4.4 g of yellow solid. The product was stirred with acetone before methanol was added to give 3.9 g (85%) of crystals mp 201° C., dec. Recrystallization from acetone-methanol gave 3.6 g, mp 205° C. dec; $^1$H NMR (acetone-d$_6$): 3.85 (m, 4H), 5.10 (t, 4H), 9.10 (broad, NH), 9.50 (s, 2H). IR (KBr): 3330(NH), 1650(ONO$_2$), 1625, 1610 (C=N), 1550, 1340 (NO$_2$). Anal. Calcd. for C$_{18}$H$_{12}$N$_{12}$O$_{19}$: C, 30.87; H, 1.73; N, 24.00. Found: C, 31.30; H, 1.76; N, 23.79.

EXAMPLE 9

2,5-bis(3,5-dimethoxyphenyl)-1,3,4-oxadiazole

A mixture of 20.5 g (0.057 mole) of N,N'-bis(3,5-dimethoxybenzoyl)hydrazine in 125 ml of phosphorus oxychloride was heated to reflux temperature. All material dissolved after a short time and the solution was held at reflux for 1 hr. before it was cooled and slowly poured into water. The damp precipitate was stirred with 250 ml of boiling methanol before the mixture was cooled and filtered to give 16.3 g (84%) of crude 2,5-bis(3,5-dimethoxyphenyl)-1,3,4-oxadiazole, mp 167°–170° C.; Crystallization of a small sample from methanol gave mp 173°–175° C. $^1$H NMR(acetone-d$_6$): 3.98 (s, 12H), 6.83 (m, 2H), 7.43 (m, 4H). Anal. Calcd. for C$_{18}$H$_{18}$N$_2$O$_5$: C, 63.15; H, 5.30; N, 8.18. Found: C, 62.73; H, 5.34; N, 7.98.

EXAMPLE 10

2,5-bis(3,5-dimethoxy-2,6-dinitrophenyl)-1,3,4-oxadiazole

A solution formed by slowly adding 54 ml of 90% nitric acid to 162 ml of concentrated sulfuric acid was cooled to 0° C. in an ice-salt bath. With good stirring, 16.2 g (0.047 mole) of crude 2,5-bis(3,5-dimethoxyphenyl)-1,3,4-oxadiazole was added in small portions over 30 min. The mixture was allowed to warm to 20° C. over 45 min., then held at 20° C. for 45 min. before it was poured onto ice to give a solid. The damp solid was stirred with boiling acetone to give 20.0 g (81%) of crude product, mp 308° C., dec. A small sample was digested with boiling methyl isobutyl ketone to raise the melting point to 315° C., dec; $^1$H NMR (DMSO-d$_6$): 4.20 (s, 12H), 7.63 (s, 2H), Anal. Calcd. for C$_{18}$H$_{14}$N$_6$O$_{13}$: C, 41.39; H, 2.70; N, 16.09. Found: C, 41.32; H, 2.83; N, 16.16.

EXAMPLE 11

2,5-bis(3,5-dimethoxy-2,4,6-trinitrophenyl)-1,3,4-oxadiazole

Nitric acid (90%) (40 ml) was slowly added with cooling to 120 ml of 30% fuming sulfuric acid and the resulting solution was stirred at 25° C. during the addition of 10.0 g (0.019 mole) of 2,5-bis(3,5-dimethoxy-2,6-dinitrophenyl)-1,3,4-oxadiazole. The mixture was slowly heated to 45° C. and held at 45°–47° C. for 5 hr. before it was cooled and poured onto ice to give a gummy solid which was stirred with methanol to produce 3.6 g of insoluble solid, mp 208° C. dec. Recrystallization from acetone-methanol gave 3.1 g (27%) of cream colored crystals mp 223° C. dec; $^1$H NMR (acetone-d$_6$): 4.28 (s); IR(KBr): 1610 (C=N), 1570, 1365(NO$_2$). Anal. Calcd. for C$_{18}$H$_{12}$N$_8$O$_{17}$: C, 35.31; H, 1.97; N, 18.30. Found C, 35.43; H, 1.91; N, 18.33.

EXAMPLE 12

2,5-bis[3,5-bis(hydroxyethylamino)-2,4,6-trinitrophenyl]-1,3,4-oxadiazole

A solution of 0.65 g (0.0106 mole) of ethanolamine in 40 ml of methanol was stirred in an ice bath while 1.55 g (0.00253 mole) of 2,5-bis(3,5-dimethoxy-2,4,6-trinitrophenyl)-1,3,4-oxadiazole was added. After 1 hr. at 0° C., the mixture was stirred for 5 hr. at room temperature before the insoluble solid (1.6 g, mp 230° C. dec.) was removed. The product was dissolved in dimethyl sulfoxide and methanol was added to give 1.4 g (76%), mp 237° C., $^1$H NMR (DMSO-d$_6$+D$_2$O): 3.12 (m, 8H), 3.63 (m, 8H). Anal. Calcd. for C$_{22}$H$_{24}$N$_{12}$O$_{17}$: C, 36.27; H, 3.32; N, 23.07. Found: C, 36.61; H, 3.32; N, 23.13.

EXAMPLE 13

2,5-bis[3-(hydroxyethylaminonitrate)-5-(hydroxyethylnitraminonitrate)-2,4,6-trinitrophenyl]-1,3,4-oxadiazole (V)

To 12 ml of 90% nitric acid stirred at −25° C. was added 1.3 g (0.00178 mole) 2,5-bis[3,5-bis(hydroxyethylamino)-2,4,6-trinitrophenyl]-1,3,4-oxadiazole. After 30 min. at −25° C., the solution was poured onto ice to give 1.77 g (100%) of yellow solid. The product was crystallized from acetone-methanol to give 1.6 g (90%) of yellow crystals, mp 193° C. dec.; $^1$H NMR(acetone-d$_6$): 3.80 (t, 4H), 4.63 (m, 4H), 5.02 (m, 8H). Anal. Calcd. for C$_{22}$H$_{18}$N$_{18}$O$_{29}$: C, 26.46; H, 1.86; N, 25.25. Found: C, 26.76; H, 1.82; N, 25.12.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A polynitroaromatic nitrate ester which is 2,4,6-trinitro-1-(2-hydroxyethylamino)-3-(2-hydroxyethylnitramino)benzenedinitrate, 2,4,6-trinitro-1,3,5-tris(2-hydroxyethylamino)benzenetrinitrate, 2,2',4,4',6,6'-hexanitro-3-(2-hydroxyethylnitramino)stilbenenitrate, 2,5-bis[3-(hydroxyethylaminonitrate)-2,4,6-trinitrophenyl]-1,3,4-oxadiazole, or 2,5-bis[3-(hydroxyethylaminonitrate)-5-(hydroxyethylnitraminonitrate)-2,4,6-trinitrophenyl]-1,3,4oxadiazole.

2. The nitrate ester of claim 1 which is 2,4,6-trinitro-1-(2-hydroxyethylamino)-3-(2-hydroxymethylnitramino)benzenedinitrate.

3. The nitrate ester of claim 1 which is 2,4,6-trinitro-1,3,5-tris(2-hydroxyethylamino)benzenetrinitrate.

4. The nitrate ester of claim 1 which is 2,2',4,4',6,6'-hexanitro-3-(2-hydroxyethylnitramino)stilbenenitrate.

5. The nitrate ester of claim 1 which is 2,5-bis[3-(hydroxyethylaminonitrate)-2,4,6-trinitrophenyl]-1,3,4oxadiazole.

6. The nitrate ester of claim 1 which is 2,5-bis[3-(hydroxyethylaminonitrate)-5-(hydroxyethylnitraminonitrate)-2,4,6-trinitrophenyl]-1,3,4-oxadiazole.

* * * * *